US006506345B1

(12) United States Patent
Lee et al.

(10) Patent No.: US 6,506,345 B1
(45) Date of Patent: Jan. 14, 2003

(54) APPARATUS FOR RAPID MEASUREMENT OF AEROSOL BULK CHEMICAL COMPOSITION

(75) Inventors: Yin-Nan E. Lee, East Setauket, NY (US); Rodney J. Weber, Atlanta, GA (US)

(73) Assignee: Brookhaven Science Associates, Upton, NY (US)

( * ) Notice: Subject to any disclaimer, the term of this patent is extended or adjusted under 35 U.S.C. 154(b) by 129 days.

(21) Appl. No.: 09/679,704

(22) Filed: Oct. 5, 2000

(51) Int. Cl.$^7$ .................................................. B01L 3/02
(52) U.S. Cl. ........................ 422/100; 422/83; 422/73; 422/81; 422/68.1; 436/146; 436/174; 73/28.01
(58) Field of Search ................................. 436/146, 174, 436/179, 181; 422/83, 73, 81, 100, 68.1; 73/28.01, 28.04, 28.05, 61.66

(56) References Cited

U.S. PATENT DOCUMENTS

| | | |
|---|---|---|
| 4,868,398 A | 9/1989 | Mulcey et al. |
| 5,855,652 A | 1/1999 | Talley |

OTHER PUBLICATIONS

Buhr, S.M., M.P. Buhr, F.C. Fehsenfeld, J.S. Holloway, U. Karst, R.B. Norton, D.D. Parrish, and R.E. Sievers, "Development of a semi–continuous method for the measurement of nitric acid vapor and particulate nitrate and sulfate," *Atmos. Environ.* 29: 2609–2624 (1995).

Carson, P.G., K.R. Neubauer, M. V. Johnston, and A.S. Wexler, "On–line chemical analysis of aerosols by rapid single–particle mass spectrometry," *J. Aerosol Sci.* 26: 535–545, (1995).

Chow, J.C., "Measurement methods to determine compliance with ambient air quality standards for suspended particles," *J. Air Wast Mang.* 45: 320–382, (1995).

Hinz, K.P., R. Kaufman, and B. Spengler, "Laser–induced mass analysis of single particles in the airborne state, " *Analyt. Chem.* 66: 2017–2076, (1994).

Ito, K., C. C. Chasteen, H. Chung, S.K. Prouthoor Z. Genfa, and P.K. Dasgupta, "A continuous monitoring system for strong acidity in aerosols," *Anal. Chem.* 70: 2839–2847, (1998).

Jayne, J.T., D.C. Leard, X. Zhang, P. Davidovits, K.A. Smith, C.E. Kolb, and D.R. Worsnop, "Aerosol mass spectrometer for size and compositions analysis of submicron particles," *J. Aerosol Sci.*, 33:49–70, (2000).

Karlsson, A., K. Irgum, and H. Hansson, "Single–state flowing liquid film impactor for continuous on–line particle analysis," *J. Aerosol Sci.* 28:1539–1551, (1997).

Khlystov, A., G.P. Wyers, and J. Slanina, "The steam–jet aerosol collector," *Atmos.Envir.* 29: 2229–2234, (1995).

(List continued on next page.)

*Primary Examiner*—Jill Warden
*Assistant Examiner*—Sam P. Siefke
(74) *Attorney, Agent, or Firm*—Margaret C. Bogosian

(57) ABSTRACT

An apparatus and method for continuous on-line measurement of chemical composition of aerosol particles with a fast time resolution are provided. The apparatus includes a modified particle size magnifier for producing activated aerosol particles and a collection device which collects the activated aerosol particles into a liquid stream for quantitative analysis by analytical methods. The method provided for on-line measurement of chemical composition of aerosol particles includes exposing aerosol carrying sample air to hot saturated steam thereby forming activated aerosol particles; collecting the activated aerosol particles by a collection device for delivery as a jet stream onto an impaction surface; flushing off the activated aerosol particles from the impaction surface into a liquid stream for delivery of the collected liquid stream to an analytical instrument for quantitative measurement.

13 Claims, 8 Drawing Sheets

OTHER PUBLICATIONS

Knutson, E.O., and K.T. Whitby, "Aerosol classification by electrical mobility: Apparatus, theory, and applications," *J. Aerosol Sci.* 6:443–451, (1975).

Kogan, Y.I., and Z.A. Burnasheva, "Growth and measurement of condensation nuclei in a continuous stream," Russian *J. Phys. Chem.* 34: 1240–1243, (1960).

Kousaka, Y., T. Niida, K. Okuyama, and H. Tanaka, "Development of a mixing type condensation nucleus counter," *J. Aerosol Sci.* 13: 231–240, (1982).

Liu, S., and P.K. Dasgupta, "Automated system for chemical analysis of airborne particles based on corona–free electrostatic collection," *Anal. Chem.* 68: 3638–3644, (1996).

Marijinissen, J.C.M., B. Scarlett, and P.J.T. Verheijen, "Proposed on–line aerosole analysis combining size determination, laser–induced fragmentation and time–of–flight mass spectroscopy," *J. Aerosol Sci.* 19: 1307, (1988).

Marple, V.A., and K. Willeke, "Impactor design," *Atmos. Envir.* 10: 891–896, (1976).

McKeown, P.J., M.V. Johnston, and D.D. Murphy, "On–line single–particle aerosol analysis by laser desorption mass spectrometry," *Analyt. Chem.* 63: 2069, (1991).

Okuyama, K., Y. Kousaka, and T. Motouchi, "Condensational growth of ultrafine aerosol particles in a new particle size magnifier," *Aerosol Sci. and Technol.* 3:353–366, (1984).

Oms, M.T., P.A.C. Jongejan, A.C. Veltkamp, G.P. Wyers, and J. Slanina, "Continuous monitoring of atmospheric HCl, $HNO_3$, $HNO_2$, and $SO_2$ by wet–annular denuder sampling with on–line chromatographic analysis," *Intern. J. Anal. Chem.* 2: 207–218, (1997).

Poruthoor, S.K., and P.K. Dasgupta, "Automated particle collection and analysis. Near–real time measurement of aerosol cerium (III)," *Analytica Chemica Acta* 361: 151–159, (1998).

Prather, K.A., T. Nordmeyer, and K. Salt, "Real–time characterization of individual aerosol particles using time–of–flight mass spectrometry," *Analyt. Chem.* 66: 1403, (1994).

Rader, D.J., and V.A. Marple, "Effect of ultra–stokesian drag and particle interception on impaction characteristics," *Aerosol Sci. Technol.* 4: 141–156, (1985).

Reents, W.D.J., A.M. Mujsce, A.J. Muller, D.J. Siconolfi, and A.G. Swanson, "Real–time elemental analysis of individual submicron particles by laser ablation time–of–flight mass spectrometry," *J. Aerosol Sci.* 23: 263, (1995).

Simon, P.K., and P.K. Dasgupta, "Continuous automated measurement of the soluble fraction of atmospheric particulate matter," *Anal. Chem.* 67: 71–78, (1995).

Stolzenburg, M.R., and V. Hering, "A method for the automated measurement of fine particle nitrate in the atmosphere" *Environ. Sci. Technol*, submitted, (1999).

Turpin, B.J., R.A. Cary, and J.J. Huntzicker, "An in situ, time–resolved analyzer for aerosol organic and elemental carbon," *J. Aerosol Sci.* 12: 161–171, (1990).

Wang, S.C., and R.C. Flagan, "Scanning electrical mobility spectrometer," *Aerosol Sci. Technol.* 13: 230–240, (1990).

Zellweger, C., M. Ammann, P. Hofer, and Baltensperger, "NOy specification with a combined wet effluent diffusion denuder–aerosol collector coupled to ion chromatography," *Atm. Envir.* 33: 1131–1140, (1999).

Schematic diagram for mass collection efficiency calibration of the PILS coupled to a dual channel ion chromatograph.

Results of the PILS-IC Mass
Collection Efficiency Tests for Sulfate

Schematic of the PILS-IC deployed for the EPA Atlanta Supersite measurements for rapid measurements of bulk aerosol ionic species.

PILS-IC measurements of sulfate concentrations and ammonium to sulfate molar ratios recorded at the Atlanta Supersite PILS-IC measurements of the ammonium molar concentration and the calculated ammonium molar concentration necessary to neutralize the measured aerosol sulfate and nitrate.

APPARATUS FOR RAPID MEASUREMENT OF AEROSOL BULK CHEMICAL COMPOSITION

This invention was made with Government support under contract number DE-AC02-98CH10886, awarded by the U.S. Department of Energy. The Government has certain rights in the invention.

BACKGROUND OF THE INVENTION

1. Field of Invention

The invention relates to an apparatus for rapid automated on-line continuous measurement of chemical composition of ambient aerosol particles. This invention also relates to a method of analyzing the chemical composition of ambient aerosol particles.

2. Description of Related Art

There have been many devices built and many processes developed to understand the sources, atmospheric transformation, fate and health effects of ambient aerosols. All require knowledge of particle chemical composition. Most processes using these devices are quantitative composition measurements, typically performed off-line on particles collected onto substrates by filtration or inertial impaction. Samples collected on the substrates are then manually extracted and analyzed. For example, measurements of ionic aerosol components involve collection on denuder-filter pack assemblies, extraction of the collected aerosol into water, and analysis of the extract for various ionic species using an ion chromatography (IC) technique. Unfortunately, although widely used, this approach has many drawbacks. Additionally, depending on flow rates and ambient concentrations, the sampling intervals are long, typically hours to days. Faster measurements are possible but often impractical due to the labor involved in filter preparation and sample extraction. This is particularly true in long-term air quality monitoring programs. Since the turn-around time for processed results also tends to be long, immediate insight and interpretation of these results are generally not available for in-the-field adjustment and modifications of experiment sampling strategies and protocols.

In addition, off-line techniques are also prone to potential sampling artifacts, particularly for volatile aerosol components. Artifacts that lead to measurement errors are due to particle/gas, particle/particle, gas/substrate, and particle/substrate interactions (Chow, 1995). These interactions occur because particles are removed from the gas, concentrated on the substrate, and then exposed to different conditions for extended periods during sampling and storage. During sampling, volatile chemical components can be adsorbed or lost as result of changes in temperature, relative humidity, and ambient particle and gas composition. Pressure drops within the sampler can also contribute to volatility losses. These artifacts have led to complicated filter pack sampling systems using multiple filters of various types to capture volatile aerosol components. Artifacts may also be introduced in the preparation and extraction of filters. Combined, these processes can lead to significant uncertainties, particularly when measuring mass concentrations of volatile or easily contaminated aerosol chemical components, such as nitrate, ammonium, and semi-volatile organic species.

Advanced instruments for real-time size-resolved measurements of particle chemical composition involving mass spectrometers have been developed (Carson et al., 1995; Hinz et al., 1994; Jayne et al., 1998; Marijinissen et al., 1988; McKeown et al., 1991; Prather et al., 1994; Reents et al., 1995). These techniques provide important insights into particle composition at single particle resolution. Unfortunately, they tend to be complex and costly, and the measurements generally do not give quantitative information on particle composition.

Other approaches involving automated bulk composition measurements have been developed. These approaches provide faster measurements and minimize some of the sampling artifacts associated with the off-line techniques. Although they do not provide size-resolved information as do mass spectrometer-based instruments, these approaches are quantitative. One common approach is to convert the aerosol particles to a vapor and measure selected evolved gases. For example, Turpin et al. (1990) developed a technique for carbonaceous aerosols by measuring the quantity of carbon dioxide produced when a loaded filter is heated to various temperatures. Stolzenburg and Hering (1999) developed an instrument that collects particles by impaction and measures various evolved gases when the deposited aerosol is flash vaporized. This approach has been successfully used to measure nitrate, and also shows promise for sulfate and carbonaceous aerosol components.

Other devices have been developed that bypass the filter or impactor sampling used in the off-line approaches for measurement of aerosol ionic species. In this case, the same analytical technique is employed, except the particles are collected directly into a liquid for automatic analysis by ion chromatography. Techniques for capturing the particles vary. Automated systems have been developed that collect particles onto a filter that is periodically washed (Buhr et al., 1995), or particles are directly impacted into a flowing liquid (Karlsson et al., 1997). In another approach, ambient particles are first grown to large water droplets by mixing with air saturated with water vapor. The large droplets are then captured onto surfaces by various inertial techniques, and combined with condensed water vapor, produce the liquid stream for analysis. A variety of instruments have been developed using this approach (Ito et al., 1998; Khlystov et al., 1995; Liu and Dasgupta, 1996; Oms et al., 1997; Poruthoor and Dasgupta, 1998; Simon and Dasgupta, 1995; Zellweger et al. 1999). Drawbacks associated with these techniques include aerosol losses, greater complexity due to the need for sample pre-concentration, and slow time response due to the time needed to drain large wetted areas.

What is needed, therefore, is an instrument designed specifically for rapid measurement of the chemical components of ambient aerosols.

OBJECTS OF THE INVENTION

It is an object of the invention to provide an apparatus and process for automated on-line continuous measurement of ambient aerosol bulk chemical composition.

It is another object of the invention to provide an apparatus and process for rapid and quantitative on-line measurement of ambient aerosol bulk chemical composition.

It is another object of the invention to provide an apparatus and process for measurement of ambient aerosol bulk composition which is not complex and is cost effective.

SUMMARY OF THE INVENTION

The present invention, which addresses the needs of the prior art and meets the objects of the invention, provides an apparatus and a method for continuous on-line measurement of chemical composition of aerosol particles. More specifically, the apparatus includes a modified particle size magnifier containing a mixing chamber and a growth chamber in fluid communication with each other and a collection device disposed downstream and in fluid communication with the growth chamber of the particle size magnifier. The collection device is preferably an inertial impactor which has a single circular nozzle and is enclosed in a housing having an impaction surface opposite the circular nozzle. The collection device also has an inlet for drawing sample air, another inlet adapted to receive carrier water and a drain, all in fluid communication with the impactor housing.

Sample air carrying fine aerosol particles enters the mixing chamber of the particle size magnifier where hot saturated steam condenses upon the fine aerosol particles producing activated aerosol particles droplets in the growth chamber of the particle size magnifier which are then collected by inertial techniques.

A single jet inertial impactor can be used to collect the activated aerosol particles onto a vertical glass plate that is continually washed with a constant water carrier flow of 0.10 mL min$^{-1}$. The flow from the inertial impactor is divided and analyzed by a dual channel ion chromatograph (IC). In its current form, 4.3-minute integrated samples were measured every 7 minutes. The apparatus of the invention provides bulk composition measurements with a detection limit of approximately 0.1 $\mu$g m$^{-3}$ for ionic species such as chloride, nitrate, sulfate, sodium, ammonium, calcium, potassium, oxalate, acetate, and formate and methane sulfonate.

As a result of the present invention an apparatus and method are provided for rapid, on-line measurement of the ionic components of ambient aerosols. By utilizing the apparatus of the present invention the turn around time for processed results is short and immediate interpretations and insights are available for in-the-field adjustment and modifications of experiment sampling strategies and protocols. Additionally, the apparatus and method of the invention are advantageous because sampling artifacts frequently associated with off-line techniques are eliminated and the resulting measurements are quantitative.

Other improvements which the present invention provides over the prior art will be identified as a result of the following description which sets for the preferred embodiments of the present invention. The description is not in any way intended to limit the scope of the present invention, but rather only to provide a working example of the present preferred embodiments. The scope of the present invention will be pointed out in the appended claims.

DETAILED DESCRIPTION OF THE PREFERRED EMBODIMENTS

Figure 1A:
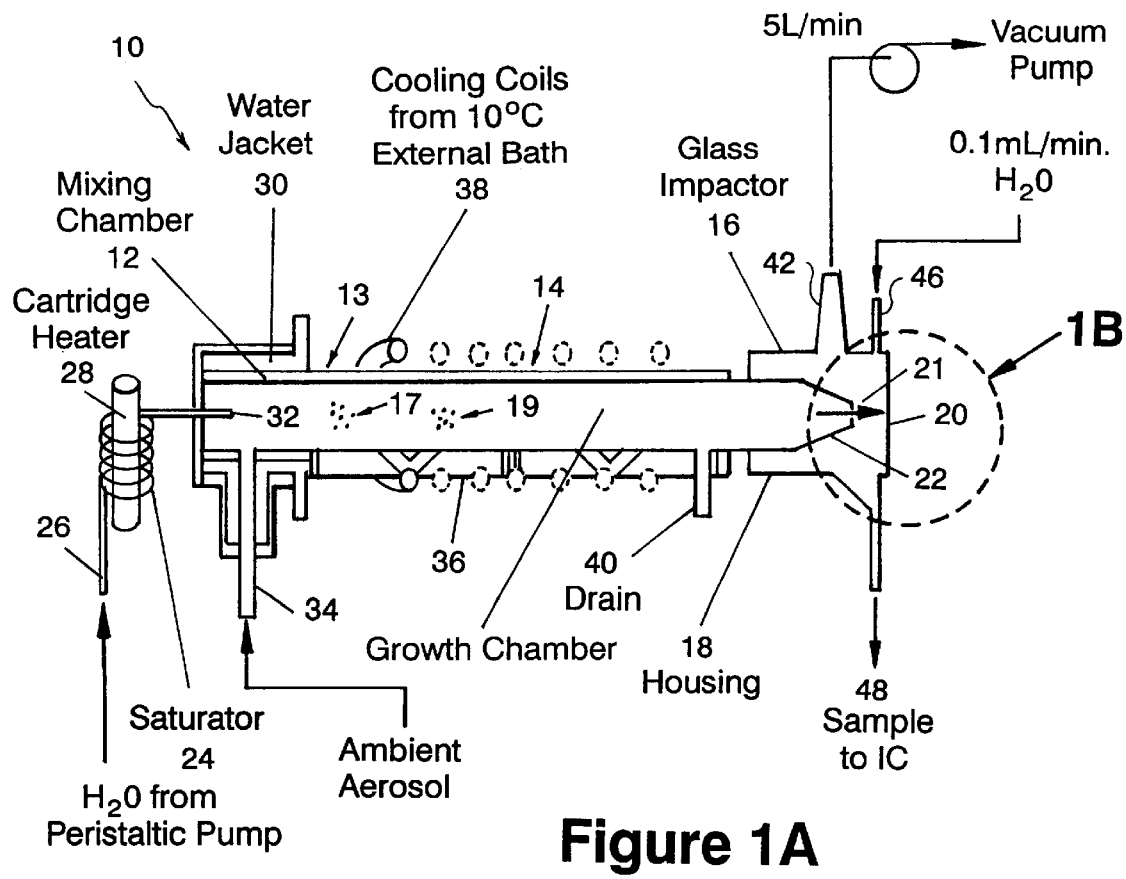
FIG. 1A is a schematic diagram of a particle-in-liquid sample (PILS) collection apparatus for rapid measurement of aerosol bulk chemical composition.

Referring now to the drawings, FIG. 1a is a schematic diagram of a preferred embodiment of the apparatus of the invention showing a particle-into-liquid sample (PILS) collector 10 for the rapid measurement of aerosol bulk chemical composition of activated aerosol droplets impacted onto a glass plate and carried by a flowing liquid stream for analysis by ion chromatography. The apparatus of the present invention comprises three main components: a mixing chamber 12 wherein sample air bearing aerosol particle is mixed with steam which condenses onto the incoming aerosol particles 17 to produce droplets bearing activated aerosol particles 19; a growth chamber 14 and a collection device 16.

As used herein "activated aerosol particles" refers to the fraction of aerosol particles entering the device that grow to large water droplets when mixed with saturated steam. The aerosol particles are then drawn into the growth chamber 14 which is disposed downstream of and in fluid communication with the mixing chamber 12 wherein the aerosol particles are allowed to grow to droplets having a diameter from about 1 micrometer to about 10 micrometers and preferably from about 2 micrometer to about 5 micrometer.

The activated aerosol particles are then collected by a collection device, preferably a single jet inertial impactor 16 which is used to collect droplets bearing the activated aerosol particles onto the vertical plate of a glass housing enclosing the inertial impactor from which, the droplets are flushed off by a constant water carrier flow into a liquid stream for transport to an analytical tool.

A variety of analytical techniques can be employed to analyze the activated aerosol carrying liquid from the impactor/collector component. Useful techniques include, without limitation, ion chromatography, capillary electrophoresis, gas chromatography, high pressure liquid chromatography, total organic carbon analyzer, and liquid particle counters.

Particle Size Magnifier

The particle growth device used in the apparatus of the invention is a modified particle size magnifier (PSM) 13. To measure accurately the total bulk aerosol composition, a particle size magnifier must activate the aerosol particles comprising the majority of the total aerosol mass. These particles must grow to sizes that can be efficiently transported, yet easily captured by an inertial impactor 16. This requires activating all particles larger than approximately 80 nm diameter, and growing them to sizes on the order of a 1 to 10 micrometer diameter.

The particle size magnifier of the invention consists of the mixing chamber 12 and the growth chamber 14. Ideally, the PSM grows particles in a supersaturated atmosphere created by adiabatic mixing of a hot saturated air stream with an ambient aerosol flow. The degree of supersaturation, which is controlled by the temperatures, saturation ratios, and mass flow rates of the hot and ambient air, determines minimum particle size activated and the amount of vapor available for condensation.

With further reference to FIG. 1A, the PILS 10 further comprises a saturator 24 which produces steam required to activate and grow the fine aerosol particles present in the sample ambient air. Here, the saturator was a ⅛-inch stainless tube 26 through which a steady flow of purified water is pumped. This tubing was coiled around a temperature-controlled cartridge heater 28. The output of steam temperature and flow is controlled by changing the temperature and the water feed flow rate control. A water flow rate from about 0.4 mL min$^{-1}$ to about 0.5 mL min$^{-1}$ can be used to generate the steam when the sample air flow rate is 5 liter per minute. The steam was injected into the PILS mixing chamber 12 through a first inlet 32 and immediately encountered the ambient air carrying aerosol particles 17 drawn in from the side through a second inlet 34 at a rate of 5 L min$^{-1}$. Ideally, rapid mixing of the hot saturated flow with the cooler aerosol flow created the supersaturated atmosphere needed for particle activation and growth.

To minimize potential volatility loss associated with altering the ambient aerosol temperature, sample air entering the mixing chamber 12 was held to near ambient temperature by a temperature controlled water jacket 30. To operate at higher flows, and for simplicity, the PSM mixer in a conventional device (Okuyama et al., 1984) was removed and the steam and ambient flows were directed at a 90° angle to each other, and neither flow was accelerated to promote turbulent mixing. This arrangement tended to limit activation to only particles larger than about 50 nm diameter. However, for urban environmental applications, this arrangement was found to be sufficient to capture most aerosol particles having a particle diameter of 2.5 micrometers, known as PM 2.5 mass (PM is particulate matter with a diameter less than 2.5 micrometers).

Following the mixing chamber 12, the supersaturated vapor and aerosol passed through a growth chamber 14 which was preferably a cylindrical condenser. The growth chamber/condenser could be from about 10 cm to about 20 cm long having an inside diameter about 2 cm and was kept at a temperature from about 5° C. to about 15° C. temperature. The condenser 14 was preferably a 16 cm-long tube with a wall temperature kept at 10° C. by a thermostated waterjacket 36 consisting of cooling coils 38 surrounding the condenser 14. The residence time of the particles in this tube could be from about 0.25 seconds to about 0.75 seconds and was preferably approximately 0.6 seconds. The walls were cooled to maintain the supersaturation necessary for particle growth and yet remove as much water vapor as possible prior to the droplet collection region. This approach provides an important difference between our approach and other droplet growth devices. In other devices known in the art, much of the steam is condensed and added to. the total sample liquid flow (Khlystov et al., 1995; Simon and Dasgupta, 1995). As a result in the devices known in the art, the condensed liquid dilutes the collected aerosol samples. Moreover, the amount of condensation is not constant so that the total volume of liquid varies and the resulting readings of activated aerosol content must be corrected. By contrast, in the present invention, we were able to control more effectively the total liquid stream containing the captured activated aerosol particles by separating the excess water vapor from the grown aerosol droplets. The PILS was operated with the growth chamber condenser 14 horizontal so that a drain 40 at the bottom of the condenser as shown in FIG. 1A could be used to remove the excess vapor as condensate from the walls. The horizontal arrangement has the potential disadvantage of losing large droplets to settling during transport. However, measurements indicated that particles in the condenser reached final diameters of nominally 2 to 3 micrometers, resulting in few particles lost by gravitational settling during transit through the condenser.

Inertial Impactor

Figure 1B:
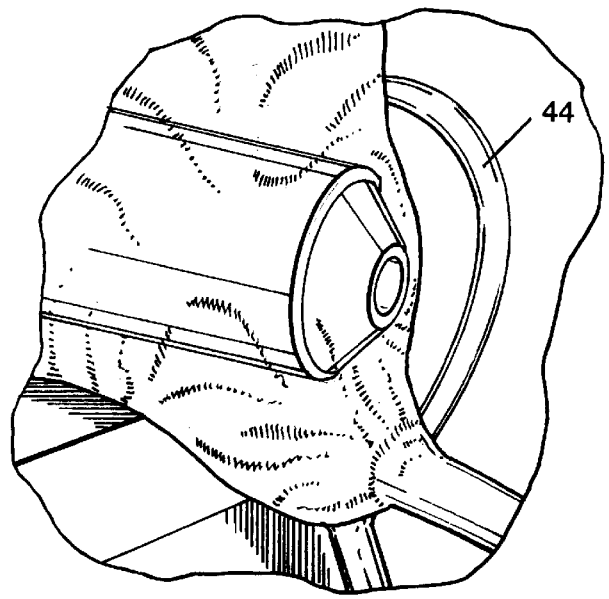
FIG. 1B is an insert showing the impactor nozzle, glass impactor housing, and stable liquid ring formed by the impinging air jet bearing activated aerosol particles onto the glass plate of the housing and a constant water flow flushing the aerosol particles off the glass plate.

With further reference to FIG. 1A, from the particle growth region the activated aerosol particles were carried by the flowing stream of sample air to an impactor/collection device 16. To collect the droplets into a flowing stream of water, sample air flow containing the activated aerosol droplets 19 was directed through the collection device, which is preferably a single circular nozzle impactor 16 which was designed for a 1 micrometer diameter cut size based on published impactor design criteria (Marple and Willeke, 1976; Rader and Marple, 1985). A jet 21 carrying activated aerosol droplets impinged onto a flat vertical glass plate 20. The vertical plate can be made of any inert material, such as glass, plastic or stainless steel and the like. It is preferable that the material be translucent, such as glass, in order to provide a visual checking of the operation of the system. The impactor nozzle 22 consisted of a 1.27 cm (0.50 inch) outside diameter (OD) stainless-steel tube with 1.04 cm (0.41 inch) inside diameter (ID) that tapered down through a 45-degree angle to a nozzle diameter of 0.119 cm (³⁄₆₄ in). Sample air was drawn through the PSM and impactor from a port 42 at the top of the impactor housing as shown in FIG. 1A. Droplets impacted onto the plate flowed radially out from the jet stagnation streamline, and at a diameter of roughly 1 cm, the liquid collected in an observable ring 44 as shown in the insert of FIG. 1B. As used herein, the jet stagnation streamline refers to an imaginary line which runs from the centerline of the jet nozzle perpendicular to and intersects the impaction plate at a point called the stagnation point. At the stagnation point the jet velocity is zero. Thus, on the impacting plate the air flowed radially away in every direction from the stagnation point. The shape of the liquid ring and its stability depended on the external dimension of the impactor nozzle 22, and the jet-to-plate distance. The latter was adjusted manually so that a stable ring was achieved. A peristaltic pump (not shown) was used to regulate the carrier water flow of 0.10 mL min$^{-1}$ introduced at the top of the ring through inlet 46. This flow drained down either side of the ring and allowed the collected drops to be flushed off the impaction surface. The resulting liquid containing the ambient activated aerosol particles flowed to a low point in the glass impaction-plate housing where it is continually pumped off to an analytical device. The liquid ring on the glass impactor surface provided a convenient visual gauge of the impactor operation; it showed that the liquid was not splashing and that a minimal wetted area was achieved, both of which were essential for a highly time resolved quantitative measurement.

Liquid Transport

The liquid sample collected at a base drain 48 of the impaction plate housing was pumped out at a rate faster than the rate at which it accumulated resulting in entrainment of air bubbles into the liquid stream. The bubble segments thus formed helped to minimize the axial mixing of the sample liquid during transport, thereby improving the time resolution of the analysis. Prior to injecting into the IC, the bubbles were removed by a debubbler (not shown in FIG. 1A) consisting of a glass tee in which the intersection was expanded to a volume of roughly 0.25 cm$^3$. The air bubbles, along with a small fraction of the sample liquid, were pumped off from the top leg, and the sample liquid, free of air, was transported to the IC at approximately 0.07 mL min$^{-1}$ from the bottom. This flow was then split and directed into two 150 µl sample-loops for injection into a duel channel ion chromatographer. The time to fill a sample loop is the integration time of the ambient air sample. With a liquid flow rate of 0.1 mL min$^{-1}$ through the sample loops, the time required to fill the sample loop was 4.3 minute integrated samples. In all cases, 0.159 cm (1/16 inch) OD Teflon tubing with 0.051 cm (0.02 inch) ID was used to transport the liquid. The small ID minimized the time for liquid transport from the aerosol collector to the IC sample loops.

Ion Chromatography Analysis

The concentrations of the major inorganic ionic components of the collected aerosol samples were analyzed using a computer-controlled dual channel ion chromatograph (Dionex, Model 300DX, Dionex Corporation, Sunnyvale, Calif.) which permitted both the cations and anions to be determined on-line and continuously. Each analysis channel consisted of a 6-port valve injector fitted with a 150 µL sample loop, a dual piston pump, an analytical separation column (IonPac CS12A, 4×250 mm, for cations; IonPac AS11, 4×250 mm, for anions, both from Dionex), a membrane suppressor, and a conductivity meter. The analysis was performed with isocratic elution using a 40 mN $H_2SO_4$ eluant for the cations and a 7.0 mN NaOH eluant for the anions, both at a flow rate of 1.0 mL min$^-$. The analysis was automated using a computer interface (Dionex, Model AC1450) and the associated software running on a PC which controlled the sample injection, data collection, data storage and chromatographic analysis. This arrangement resulted in approximately 7-minute long chromatograms for both anions and cations. This 7-minute duty cycle was the limiting factor controlling the sampling frequency. The IC system was calibrated daily using standard solutions of four different concentrations of all the ions being analyzed.

In these instruments, the total sample liquid flow must be known to calculate the concentrations of the chemical components of the ambient aerosol. Although the carrier water flow rate was known, the amount of additional volume introduced by the collected water droplets was not directly measured. However, tests showed the final sample liquid flow remained fairly constant (±3%) for ambient aerosol concentrations ranging from 5000 to 10000 cm$^{-3}$, well within the range of ambient concentrations studied at the Atlanta EPA Supersite. ps Measurement Uncertainties and Limit of Detection The limit of detection (LOD) and uncertainty of the particle-into-liquid sample collector-ion chromatograph system (PILS-IC) can be estimated from the expected sensitivity of the ion chromatograph (IC) and measured flow rates of the sample air and liquid stream. With an IC sensitivity of roughly 0.1 µM for nitrate, sulfate, sodium, ammonium, calcium and potassium, a sample flow rate of 5 L min$^{-1}$, a carrier liquid flow of 0.10 mL min$^{-1}$, the PILS-IC was estimated to have a limit of detection near 0.1 µg m$^{-3}$ for these ionic components. The uncertainty associated with the mass measurements was estimated by combining the uncertainties in flow rates and IC calibrations. Uncertainties of both liquid and air flow rates were approximately ±4%. Uncertainties in the IC calibration for sulfate, nitrate, and ammonium were determined by comparisons with measurements of independent National Institute of Standards and Technology (NIST) traceable standards (Fisher Scientific). Comparisons immediately follow IC calibrations were within 3 to 5%, and 5 to 10% after running for an extended period. The overall uncertainty of the measured ionic species is estimated to be ±10%.

Particle Collection Efficiency

Figure 2:
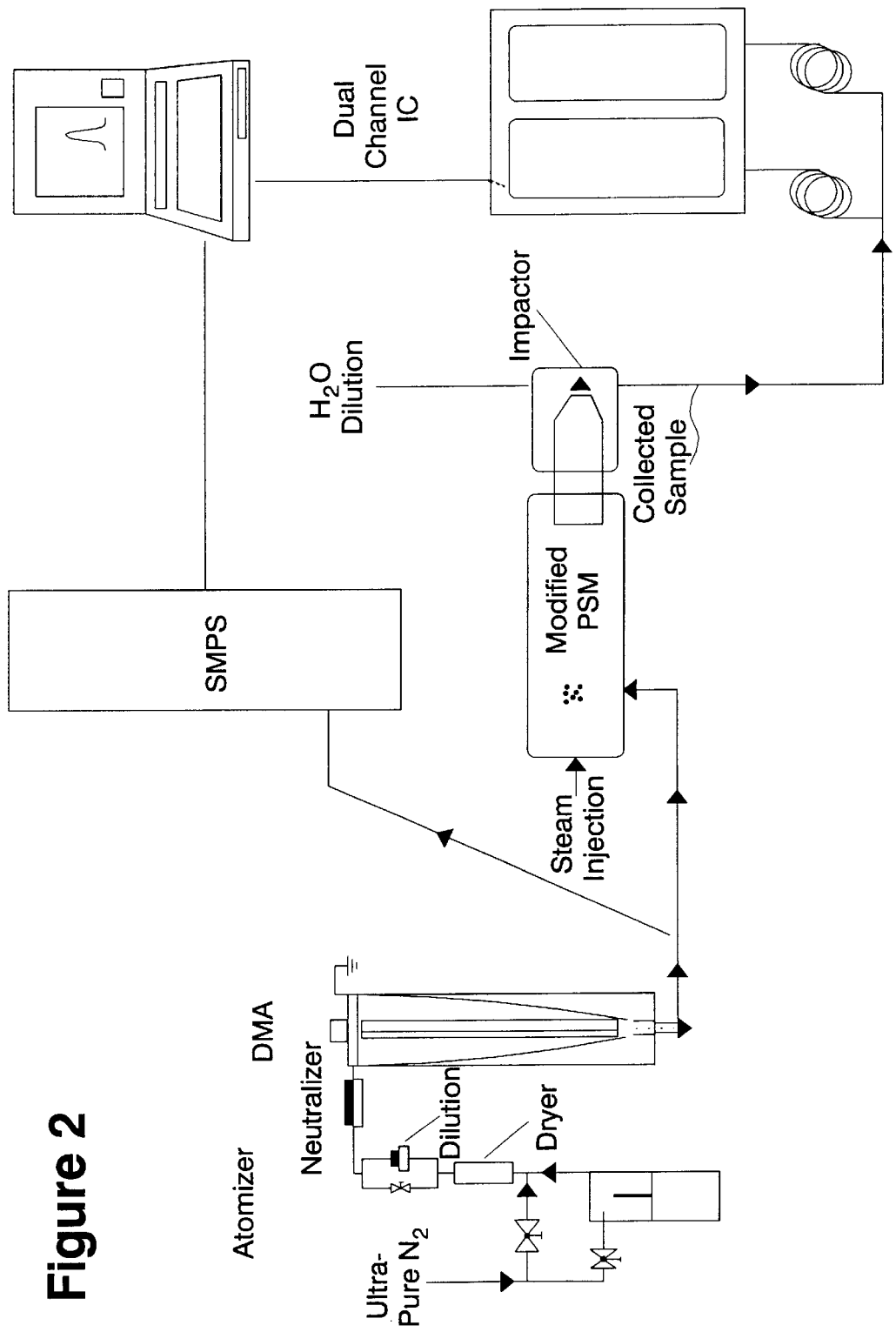
FIG. 2 is a schematic diagram of a system used for mass collection efficiency calibration of the PILS coupled to a dual ion chromatograph.
Figure 3:
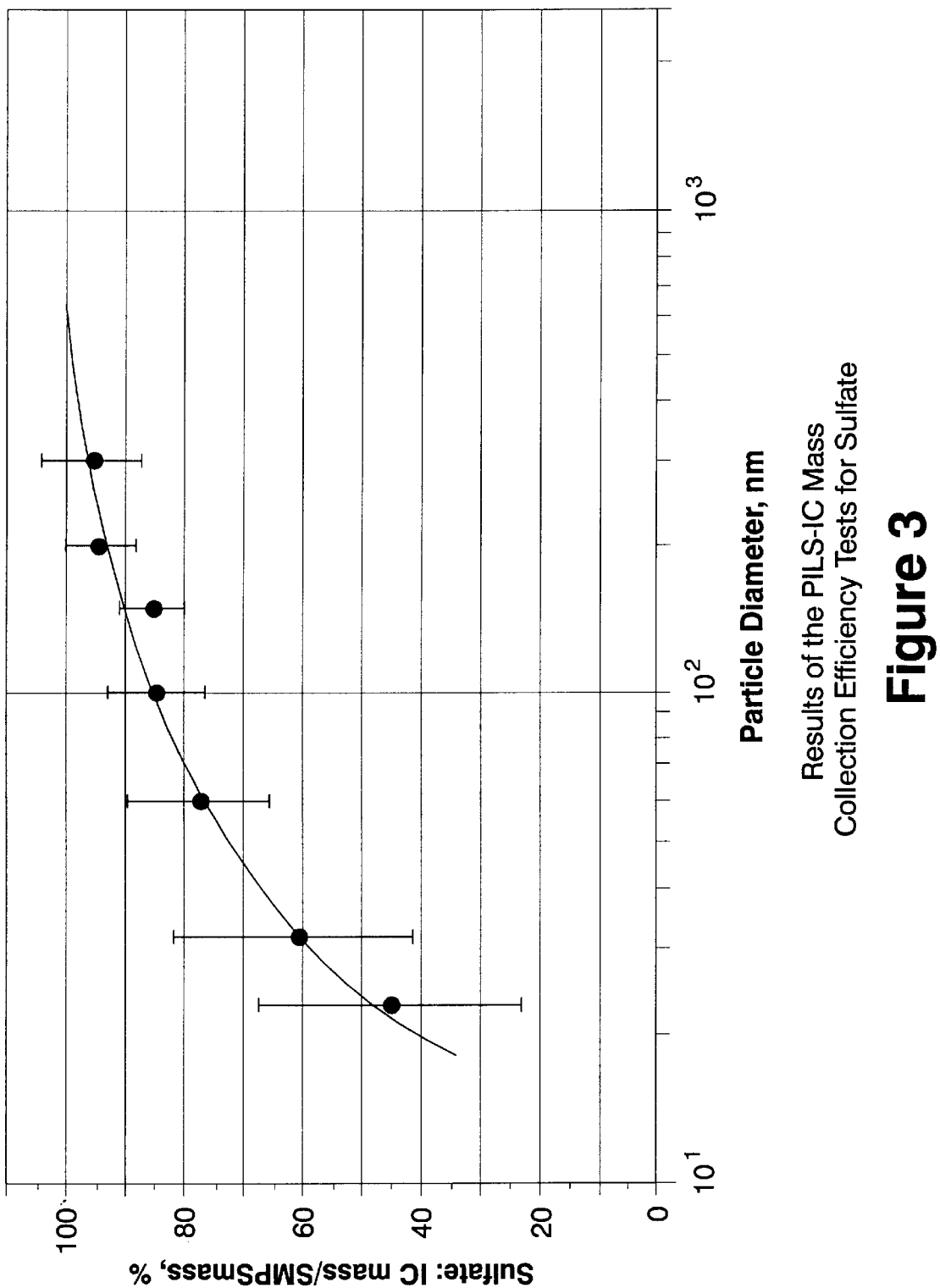
FIG. 3 is a graph illustrating results of the particle-in-liquid sample-ion chromatograph (PILS-IC) mass collection efficiency tests for sulfate.

To determine the minimum size of particles activated, and the overall droplet transport and collection efficiency, the mass collection efficiency of the PILS was determined in the laboratory. In these calibration experiments, aerosol particles of known chemical composition and size were generated using the standard technique of atomizing an aqueous solution, neutralizing and diffusion drying the aerosol, and selecting a specific size with a differential mobility analyzer (DMA) (Knutson and Whitby, 1975) (FIG. 2). The mass concentration of the calibration aerosol was measured with the PILS-IC and compared to the mass concentration measured with a scanning mobility particle spectrometer (SMPS) as provided by TSI Inc, St Paul Minn., (Wang and Flagan, 1990). It is noted that the SMPS measured the particle number distribution. This number was converted to total aerosol mass concentration from the known particle density and by assuming that the particles were dry. This was a valid assumption since the relative humidity (RH) of the calibration aerosol was about 20%, well below the efflorescence point of 40% RH for a calibration aerosol of ammonium sulfate ($(NH_4)_2SO_4$). The SMPS measurement also accounted for single and multiple charged particle contributions to total mass. Calibration results for sulfate generated from $(NH_4)_2SO_4$ are shown in FIG. 3. Measured concentration ratios were compared to the size of the single charged particle generated. It is noted that at the smaller sizes where concentration ratios were sensitive to size, contributions of multiply charged particles to the total mass were small since most particles were singly charged. Selected calibration particle diameters ranged from 25 to 300 nm with total number concentrations varying between 150 and 10$^5$ particles cm$^{-3}$, depending on particle size. These concentrations corresponded to sulfate mass concentrations between 0.5 and 40 µg m$^{-3}$, typical of ambient urban aerosol concentrations.

From FIG. 3, a maximum collection efficiency of 94% was measured, and over 80% of all particles larger than approximately 50 nm were collected. Below 50 nm, the collection efficiency dropped rapidly with decreasing size. The drop in collected mass efficiency was attributed primarily to non-activation of small size particles, a result of our limited mixing of saturated water vapor and sample air. It is noted that to achieve measurable masses for the smaller particle sizes tested (i.e., 25 micrometer diameter size), number concentrations of the order of 10$^5$ particles cm$^{-3}$ were required. Since the activated drops grew to similar final sizes, during the experiments, there was a concern that unrealistically high concentrations necessary for the calibrations at the smaller sizes, could lead to underestimating the activation efficiencies due to vapor depletion. This was found, however, to have a minor effect since tests with increased steam-water flow rates had little influence on the lower size collection efficiencies. These tests demonstrated that the PILS collection efficiency was not significantly influenced by particle concentration for concentrations up to 10$^5$ cm$^{-3}$.

Although the activation efficiency shown in FIG. 3 was likely sufficient for collecting most of the ambient aerosol mass in the EPA Supersite study, an enhanced mixer could be designed to activate much smaller particles.

Results from the Atlanta EPA Supersite Study

The PILS was tested during 1999 at the Atlanta EPA Supersite experiment where a large assembly of aerosol equipment were being tested for their performance. As the first EPA Supersite, our experiments were aimed at inter-comparing various techniques for measuring chemical composition of particles smaller than 2.5 micrometer diameter, so-called PM2.5. A secondary goal was to study the chemical and physical properties of urban PM2.5 aerosol particles in the southeastern United States. Preliminary results showed that the PILS agreed well with other semi-continuous techniques, and were in general agreement with filter measurements of non-volatile species, such as sulfate.

Figure 4:
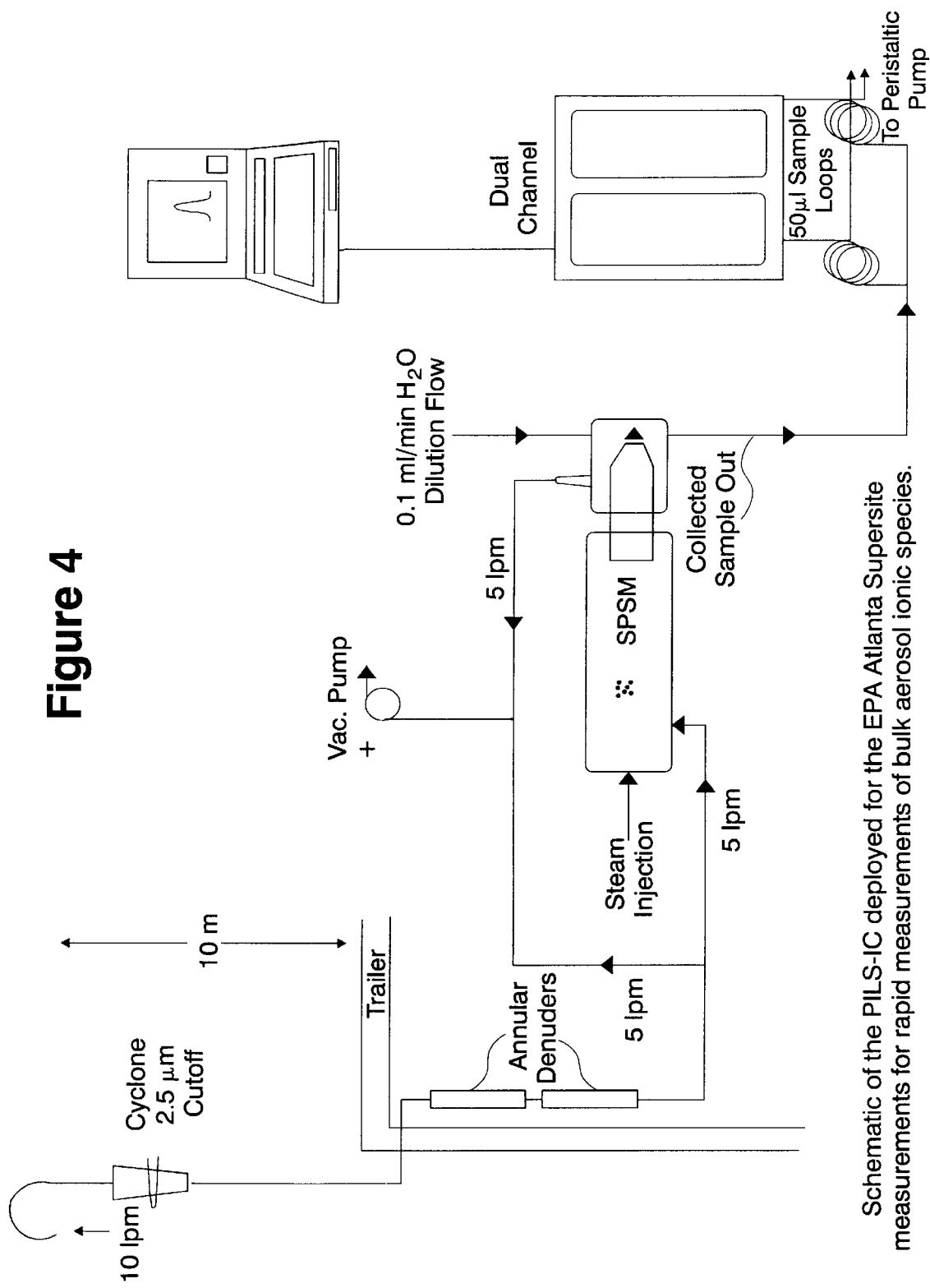
FIG. 4 is a schematic diagram illustrating the use of PILS-IC at the EPA Atlanta Supersite for rapid measurements of bulk aerosol ionic species.

The particles bearing diameter less than 2.5 micrometer (PM2.5) for sampling system, including the PILS-IC, are shown in FIG. 4. The sampling inlet consisted of an inverted stainless steel tube connected to a 10 L min$^{-3}$, 2.5 micrometer cut URG (University Research Glass) cyclone to permit measurements of PM2.5. Inside the sampling trailer, the 10 L min$^{-3}$ aerosol flow passed through two URG annular denuders in series, one coated with citric acid and the other calcium carbonate, to remove gaseous $NH_3$, and $SO_2$ and $HNO_3$ respectively. The denuders were regenerated approximately every 2 days.

Figure 5:
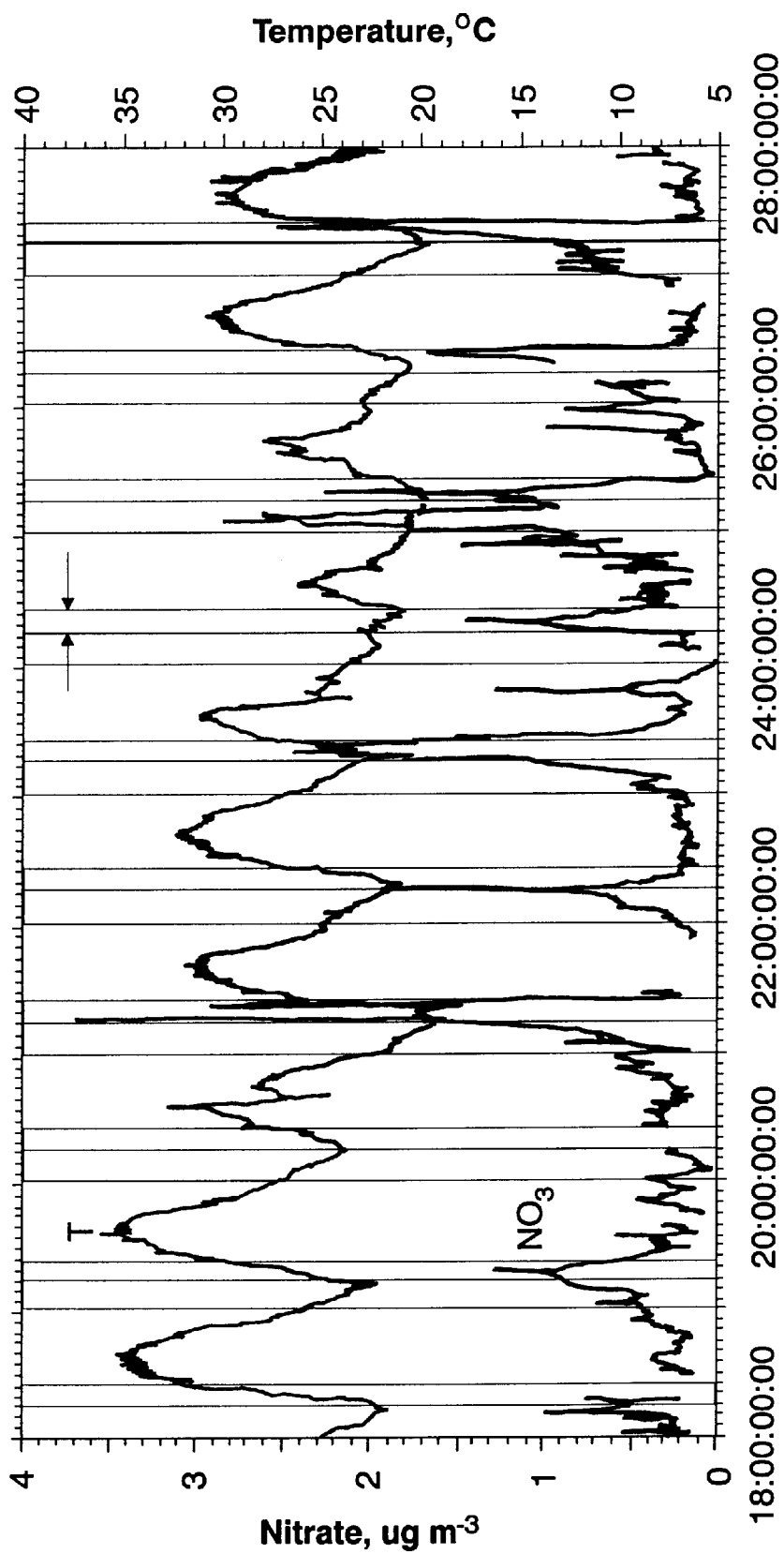
FIG. 5 is a graph illustrating PILS-IC measurements of nitrate ($NO_3^-$) and temperature (T) measured at the EPA Atlanta Supersite.
Figure 6:
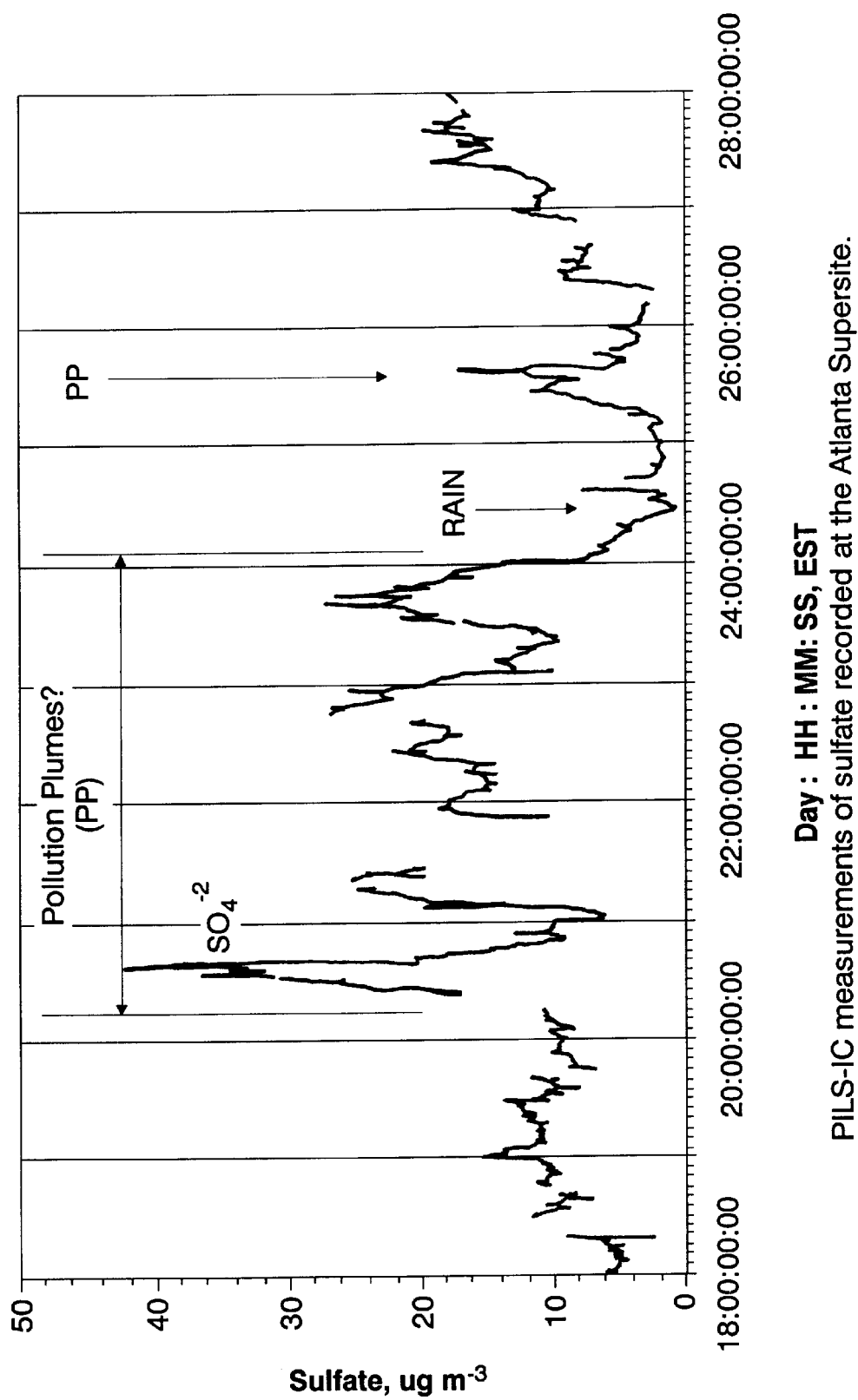
FIG. 6 is a graph illustrating PILS-IC measurements of sulfate ($SO_4^{-2}$) measured at the EPA Atlanta Supersite.
Figure 7:
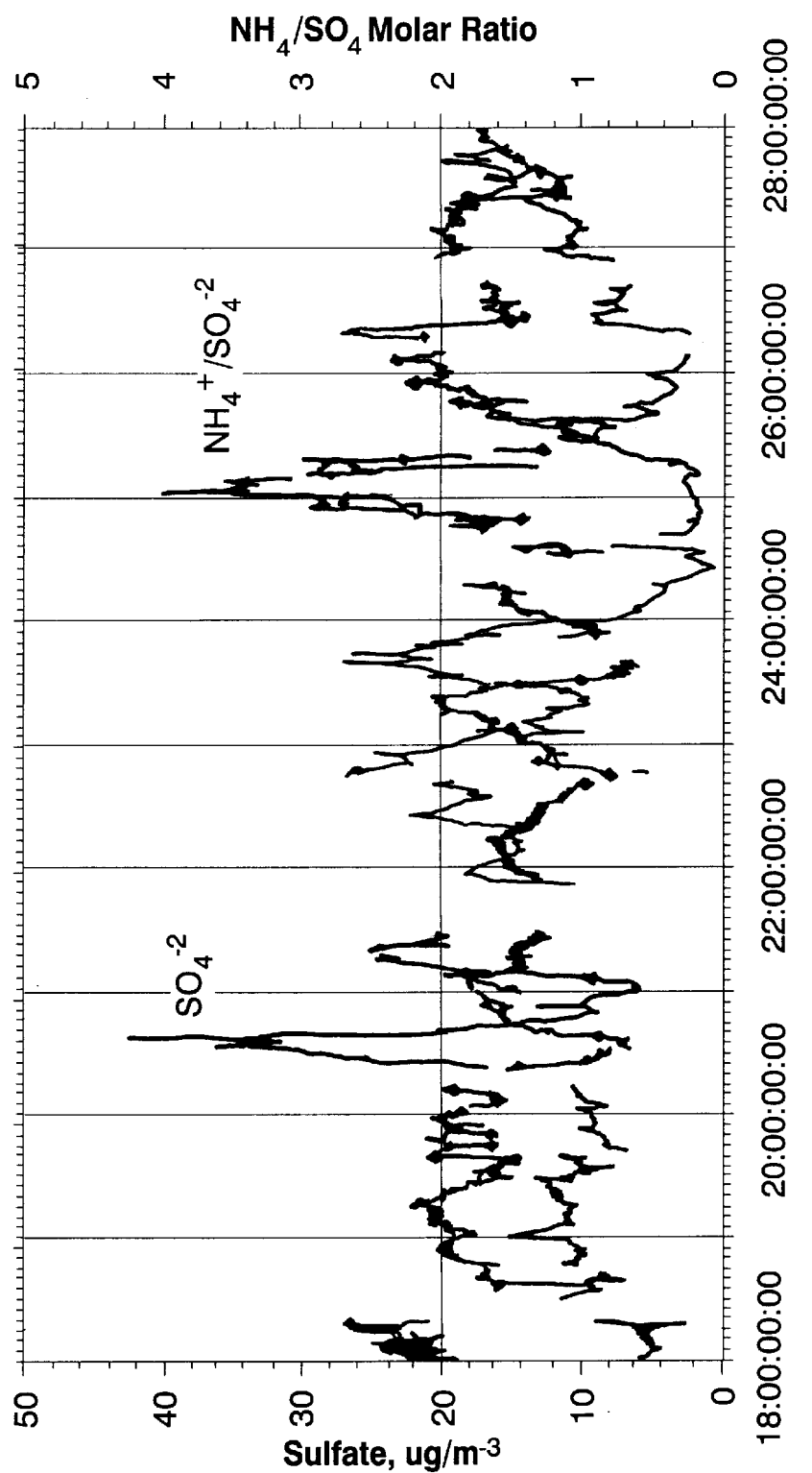
FIG. 7 is a graph illustrating PILS-IC measurements of sulfate ($SO_4^{-2}$) concentrations and ammonium to sulfate molar ratios ($NH_4^+/SO_4^{-2}$) measured at the EPA Atlanta Supersite.

Focusing on nitrate, sulfate, and ammonium, FIGS. 5, 6 and 7 show the data collected during a 10-day sample period, from Aug. 19 to Aug. 28, 1999. FIG. 5 shows nitrate levels ranging between roughly the LOD of the system, i.e., 0.1, to 3.0 $\mu$g m$^{-3}$ during this time. The nitrate measurements demonstrate how highly time-resolved measurements could provide insights into processes controlling the mass-loadings and chemical compositions of ambient aerosol. FIG. 5 shows that on practically every day, nitrate peaked in early morning between 600 and 1000 Eastern Standard Time. Although this coincides with the morning rush hour, peaks were also observed on Saturday and Sunday when there is no rush hour traffic. These peaks correlate with periods of minimum daily temperatures, which are also times of maximum relative humidity. It is known that partitioning of nitric acid between the gas and condensed phase is highly sensitive to temperature, RH, and aerosol composition. Consistent nitrate peaks following minimum temperatures and maximum daily RH indicate that these thermodynamic effects played a major role in the formation of the early morning nitrate peaks.

During the period of August 18 to August 28, other ancillary measurements showed that total PM2.5 mass concentrations varied between 5 to 50 $\mu$g m$^{-3}$ as measured by the tapered element oscillating microbalance instrument ("TEOM") with inlet heated to 50° C., as provided by Rupprecht and Patashnick Co., Albany N.Y. (Bergin, personal communication). As is typical of the eastern United States, sulfate was found to be a major component and nitrate a minor component of the total PM2.5 aerosol mass. FIG. 6 shows the sulfate concentration measured during this period. Sulfate concentrations ranged from about 2 to 40 $\mu$g m$^{-3}$, with highest levels corresponding to pollution episodes, possibly associated with power plant plumes or other local sources. During this period these plumes were observed primarily between August 20 to August 24.

Figure 8:
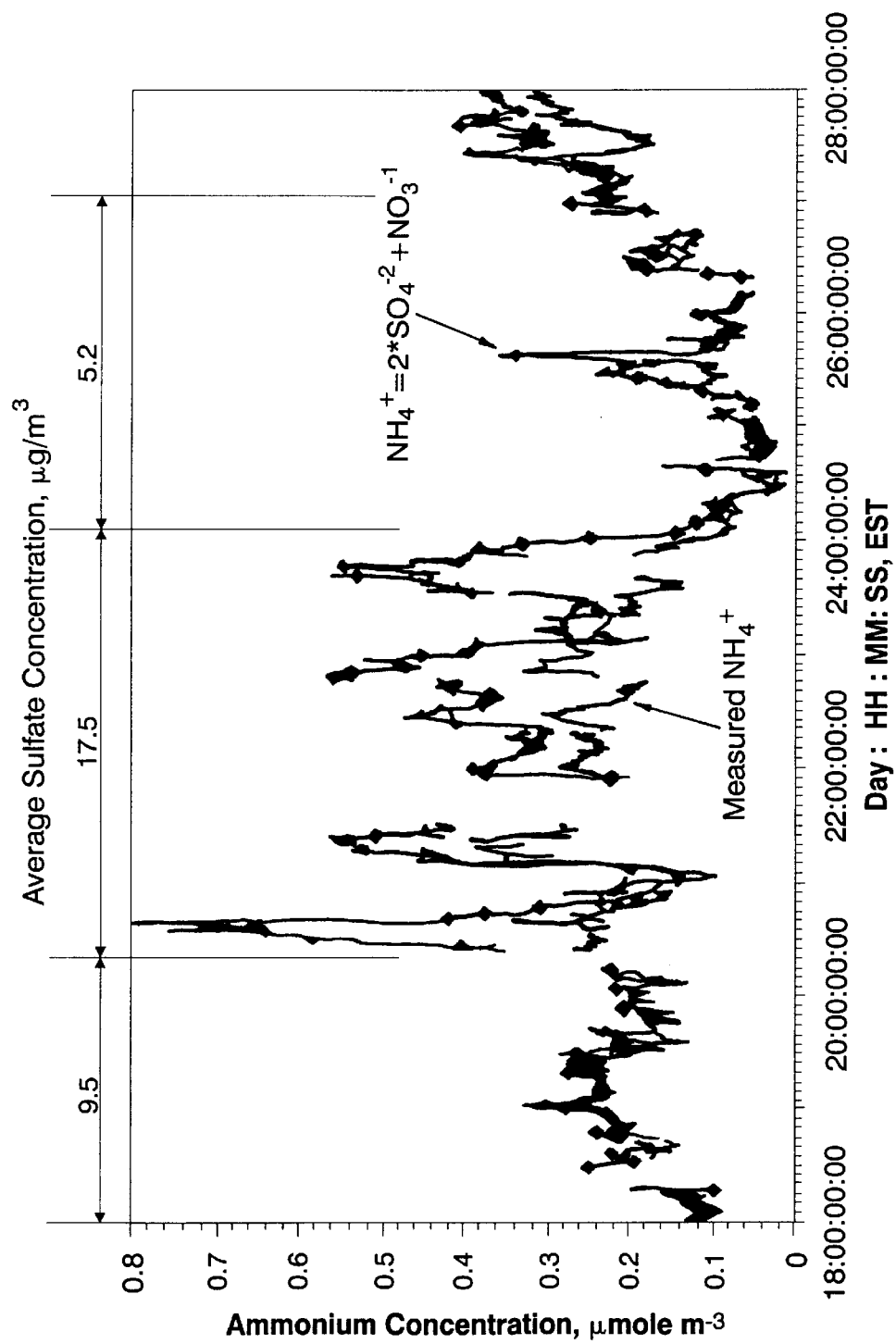
FIG. 8 is a graph illustrating PILS-IC measurements of the ammonium ion ($NH_4^+$) molar concentration and the calculated ammonium molar concentration necessary to neutralize the measured aerosol sulfate ($SO_4^{-2}$) and nitrate ($NO^-_3$) at the EPA Atlanta Supersite.

Sulfate concentration and ammonium to sulfate molar ratios are plotted in FIG. 7. The molar ratios are of interest since they provide insights into aerosol gas-to-particle conversion processes and also served as an internal check on our measurement accuracy. Under typical conditions, ammonium to sulfate molar ratios were near two, suggesting that sulfate was usually completely neutralized, assuming most of the ammonium was associated with sulfate. However, during pollution episodes, molar ratios often dropped below one, arising most likely from the fact that the available ammonia present was insufficient to neutralize the unusually large amount of sulfuric acid produced in the plume. There were also periods when molar ratios exceeded two. These typically occurred when the total aerosol mass concentrations were very low. For example, molar ratios peaked near 4 during periods near midnight on August 26 and August 27. During these times PM2.5 levels were unusually low at 10 $\mu$g m$^{-3}$. At these times ammonium may also be associated with other acidic species such as nitric acid. To test this we plotted in FIG. 8 the measured ammonium molar concentration and the concentration calculated from measured sulfate and nitrate, assuming that these acidic species are completely neutralized by ammonium. The graph shows that the measured and calculated ammonium concentrations agree remarkable well, except under high sulfate concentrations associated with pollution plumes. During these times there appears to be insufficient ammonia to neutralize the aerosol. These data attest to the accuracy of the independent anion and cation measurement results.

Discussions of Results

Our preliminary investigations with a newly designed particle-into-liquid sampler (PILS) coupled with an ion chromatograph (IC) suggest that it is a powerful tool for rapid quantitative measurements of aerosol particle ionic composition. The instrument is simple and robust. Sampling artifacts associated with filter techniques are minimized since particles are rapidly stabilized by formation of water drops collected into a flowing liquid. Data is obtained near real-time with a 4.3 minute integrated sample at a duty cycle of 7 min. With an IC sensitivity of roughly 0.1 $\mu$M, a sample flow rate of 5 L min$^{-1}$, collecting particles into a liquid flow of 0.10 mL min$^{-1}$, the PILS-IC had a limit of detection near 0.1 $\mu$g m$^{-3}$ for nitrate, sulfate, sodium, ammonium, calcium and potassium. Although, at this point we have only focused on coupling the PILS to an IC, other analytical techniques could also be employed to measure quantitatively additional aerosol components and properties.

REFERENCES

The following publications as mentioned in the foregoing specification, are incorporated herein by reference as if set forth in full for all they disclose:

Buhr, S. M., M. P. Buhr, F. C. Fehsenfeld, J. S. Holloway, U. Karst, R. B. Norton, D. D. Parrish, and R. E. Sievers (1995) Development of a semi-continuous method for the measurement of nitric acid vapor and particulate nitrate and sulfate, *Atmos. Environ.* 29: 2609–2624.

Carson, P. G., K. R. Neubauer, M. V. Johnston, and A. S. Wexler (1995) On-line chemical analysis of aerosols by rapid single-particle mass spectrometry, *J. Aerosol Sci.* 26: 535–545.

Chow, J. C. (1995) Measurement methods to determine compliance with ambient air quality standards for suspended particles, *J. Air Wast Mang.* 45: 320–382.

Hinz, K. P., R. Kaufmann, and B. Spengler (1994) Laser-induced mass analysis of single particles in the airborne state, Analyt. Chem. 66: 2017–2076.

Ito, K., C. C. Chasteen, H. Chung, S. K. Prouthoor, Z. Genfa, and P. K. Dasgupta (1998) A continuous monitoring system for strong acidity in aerosols, *Anal. Chem.* 70: 2839–2847.

Jayne, J. T., D. C. Leard, X. Zhang, P. Davidovits, K. A. Smith, C. E. Kolb, and D. R. Worsnop (1998) Aerosol mass spectrometer for size and composition analysis of submicron particles, J. Aerosol Sci., submitted.

Karlsson, A., K. Irgum, and H. Hansson (1997) Single-stage flowing liquid film impactor for continuous on-line particle analysis, *J. Aerosol Sci.* 28: 1539–1551.

Khlystov, A., G. P. Wyers, and J. Slanina (1995) The steam-jet aerosol collector, *Atmos. Envir.* 29: 2229–2234.

Knutson, E. O., and K. T. Whitby (1975) Aerosol classification by electrical mobility: Apparatus, theory, and applications, *J. Aerosol Sci.* 6: 443–451.

Kogan, Y. I., and Z. A. Burnasheva (1960) Growth and measurement of condensation nuclei in a continuous stream, Russian *J. Phys. Chem.* 34: 1240–1243.

Kousaka, Y., T. Niida, K. Okuyama, and H. Tanaka (1982) Development of a mixing type condensation nucleus counter, *J. Aerosol Sci.* 13: 231–240.

Liu, S., and P. K. Dasgupta (1996) Automated system for chemical analysis of airborne particles based on corona-free electrostatic collection, *Anal. Chem.* 68: 3638–3644.

Marijinissen, J. C. M., B. Scarlett, and P. J. T. Verheijen (1988) Proposed on-line aerosol analysis combining size determination, laser-induced fragmentation and time-of-flight mass spectroscopy, *J. Aerosol Sci.* 19: 1307.

Marple, V. A., and K. Willeke (1976) Impactor design, Atmos. Env., 10, 891–896.

McKeown, P. J., M. V. Johnston, and D. D. Murphy (1991) On-line single-particle aerosol analysis by laser desorption mass spectrometry, *Analyt. Chem.* 63: 2069.

Okuyama, K., Y. Kousaka, and T. Motouchi (1984) Condensational growth of ultrafine aerosol particles in a new particle size magnifier, *Aerosol Sci. and Technol.* 3: 353–366.

Oms, M. T., P. A. C. Jongejan, A. C. Veltkamp, G. P. Wyers, and J. Slanina (1997) Continuous monitoring of atmospheric HCL, HNO3, HNO2, and SO2 by wet-annular denuder sampling with on-line chromatographic analysis, *Intern. J. Anal. Chem.* 2: 207–218.

Poruthoor, S. K., and P. K. Dasgupta (1998) Automated particle collection and analysis. Near-real time measurement of aerosol cerium (III), *Analytica Chemica Acta* 361: 151–159.

Prather, K. A., T. Nordmeyer, and K. Salt (1994) Real-time characterization of individual aerosol particles using time-of-flight mass spectrometry, *Analyt. Chem.* 66: 1403.

Rader, D. J., and V. A. Marple (1985) Effect of ultra-stokesian drag and particle interception on impaction characteristics, *Aerosol Sci. Technol.* 4: 141–156.

Reents, W. D. J., A. M. Mujsce, A. J. Muller, D. J. Siconolfi, and A. G. Swanson (1995) Real-time elemental analysis of individual submicron particles by laser ablation time-off-light mass spectrometry, *J. Aerosol Sci.* 23: 263.

Simon, P. K., and P. K. Dasgupta (1995) Continuous automated measurement of the soluble fraction of atmospheric particulate matter, *Anal. Chem.* 67: 71–78.

Stolzenburg, M. R., and V. Hering (1999) A method for the automated measurement of fine particle nitrate in the atmosphere, Environ. Sci. Technol, submitted.

Turpin, B. J., R. A. Cary, and J. J. Huntzicker (1990) An in situ, time-resolved analyzer for aerosol organic and elemental carbon, *J. Aerosol Sci.* 12: 161–171.

Wang, S. C., and R. C. Flagan (1990) Scanning electrical mobility spectrometer, *Aerosol Sci. Technol.* 13: 230–240.

Zellweger, C., M. Ammann, P. Hofer, and U. Baltensperger (1999) NOy speciation with a combined wet effluent diffusion denuder-aerosol collector coupled to ion chromatography, *Atm. Envir.* 33: 1131–1140.

Thus, while there have been described what are presently believed to be the preferred embodiments of the present invention, those skilled in the art will realize that other and further modifications can be made to the invention without departing from the true spirit of the invention, such further and other modifications are intended to be included herein within the scope of the appended claims.

What is claimed is:

1. An apparatus for continuous on-line measurement of chemical composition of aerosol particles which comprises:

an enhanced particle size magnifier including:
a mixing chamber having a first inlet, a second inlet and an outlet, said first inlet adapted to receive steam, said second inlet adapted to receive sample air carrying aerosol particles;
a growth chamber disposed downstream of and in fluid communication with said mixing chamber for activation of said aerosol particles, said growth chamber having means for controlling the temperature of said growth chamber and means for draining excess liquid; and
a collection device for said activated aerosol particles disposed downstream of and in fluid communication with said growth chamber, said collection device having a nozzle means and a housing encapsulating said nozzle means, said housing having an impaction surface opposite said nozzle means, means for drawing sample air in communication with said housing, means adapted to receive carrier water and drain means;

said means for drawing sample air connected to a vacuum source for directing said sample air carrying said activated aerosol particles through said nozzle means to form a jet stream; said jet stream impinging said activated aerosol particles upon said impaction surface;

said means adapted to receive carrier water for flushing said impinged activated aerosol particles from said impaction surface into a liquid stream for transport to analysis.

2. The apparatus of claim 1, wherein said nozzle means and the nozzle to impaction surface distance are sized such that a stable liquid ring of water is formed from impaction of said activated aerosol upon said impaction surface.

3. The apparatus of claim 1, wherein said sample air carrying aerosol particles is drawn into said mixing chamber at about 5 L min$^{-1}$.

4. The apparatus of claim 1, wherein said steam inlet and said sample air inlet are positioned such that the steam flow and sample air flow are directed at about a 90° angle to each other.

5. The apparatus of claim 1, wherein said aerosol particles that are activated have a diameter greater than about 50 nm.

6. The apparatus of claim 1, further comprising a water jacket around said mixing chamber for maintaining ambient temperature.

7. The apparatus of claim 1, wherein said growth chamber is a condenser for removal of excess water vapor.

8. The apparatus of claim 7, wherein said condenser has a length from about 10 cm to about 20 cm.

9. The apparatus of claim 1, wherein said means for controlling the temperature of said growth chamber is a water jacket controlled by thermostat to maintain the temperature from about 5° C. to about 15° C.

10. The apparatus of claim 1, wherein said collection device is a single substantially circular nozzle impactor and said impaction surface is a substantially flat vertical plate.

11. The apparatus of claim 1, wherein said nozzle means is a conically shaped nozzle having an outer diameter of from about 0.5 inches tapering down to about 0.25 inches at a 45° angle and a nozzle to plate distance of from about 0.045 inches to about 0.050 inches and nozzle diameter of 0.047 inches.

12. The apparatus of claim 1, wherein said analysis is provided by analytical means selected from the groups consisting of ion chromatography, capillary electrophoresis, gas chromatography, high pressure liquid chromatography, total organic carbon analyzer, liquid particle counters, and liquid chromatography/mass spectrometry.

13. The apparatus of claim 1, further comprising a saturator in fluid communication with said mixing chamber for providing steam to said first inlet, said saturator comprising a stainless steal tubing adapted to receive a steady flow of purified water and a temperature controlled cartridge heater, said tubing coiled around said cartridge heater.

* * * * *